(12) United States Patent
Sacorague et al.

(10) Patent No.: US 12,650,419 B2
(45) Date of Patent: Jun. 9, 2026

(54) METHOD FOR ANALYSIS AND DETECTION OF SOLIDS IN EMULSIONS, OIL AND DERIVATIVES THEREOF

(71) Applicant: Petróleo Brasileiro S.A.—Petrobras, Rio de Janeiro (BR)

(72) Inventors: Luiz Alexandre Sacorague, Rio de Janeiro (BR); Rogerio Mesquita De Carvalho, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 875 days.

(21) Appl. No.: 17/989,051

(22) Filed: Nov. 17, 2022

(65) Prior Publication Data

US 2023/0152294 A1 May 18, 2023

(30) Foreign Application Priority Data

Nov. 18, 2021 (BR) ...................... 10 2021 023221 8

(51) Int. Cl.
*G01N 33/28* (2006.01)
*G01N 21/33* (2006.01)
(Continued)

(52) U.S. Cl.
CPC ......... *G01N 33/2835* (2013.01); *G01N 21/33* (2013.01); *G01N 21/51* (2013.01); *G01N 35/10* (2013.01); *G01N 2021/513* (2013.01); *G01N 2035/00475* (2013.01); *G01N 2035/00524* (2013.01)

(58) Field of Classification Search
CPC .... G01N 33/2835; G01N 21/33; G01N 21/51; G01N 35/10; G01N 2021/513; G01N 2035/00475; G01N 2035/00524; G01N 15/075
See application file for complete search history.

(56) References Cited

U.S. PATENT DOCUMENTS

2016/0187253 A1* 6/2016 Koseoglu ............... G01N 21/33
702/30

FOREIGN PATENT DOCUMENTS

WO WO-2017100224 A1 * 6/2017 ......... G01N 33/2876

OTHER PUBLICATIONS

Silva Jr. et al., Ultrasound Measurement of the Content of Solid Particles in Liquid Media Applied to Oil Industry, 2011, 21st International Congress of Mechanical Engineering, pp. 1-9. (Year: 2011).*
Yue et al., A review on analytical methods of petroleum hydrocarbons in water and sediment of aquatic systems, 2021, IOP Conference Series: Earth and Environmental Science, 621, pp. 1-6. (Year: 2021).*

(Continued)

*Primary Examiner* — Kathryn Elizabeth Limbaugh
(74) *Attorney, Agent, or Firm* — Morrison & Foerster LLP

(57) ABSTRACT

The present invention addresses to a method for analyzing and detecting solids in emulsions, oil and derivatives thereof even in the presence of high contents of water (>5% v/v), which is based on the absorption and scattering of light by solids suspended in solution.

The application of the method of this invention contributes to greater reliability in terms of control of BSW (oil quality) and OGC (water to be treated and discarded). Additionally, there is the possibility of controlling the dosage of products such as scale inhibitors and naphthenates inhibitors, optimizing the dosage and minimizing operational occurrences associated with the formation of deposits. These eventually lead to equipment clogging throughout the process.

7 Claims, 2 Drawing Sheets

(51) Int. Cl.
    *G01N 21/51*     (2006.01)
    *G01N 35/00*     (2006.01)
    *G01N 35/10*     (2006.01)

(56)               References Cited

OTHER PUBLICATIONS

ASTM D4807-05, Standard Test Method for Sediment in Crude Oil by Membrane Filtration, 2020, ASTM International/API, pp. 1-5. (Year: 2020).*

Borges et al., Use of near infrared for evaluation of droplet size distribution and water content in water-in-crude oil emulsions in pressurized pipeline, 2015, Elsevier, Fuel 147, pp. 43-52. (Year: 2015).*

Alvarado et al. (2011) "Stability Proxies for Water-in-Oil Emulsions and Implications in Aqueous-based Enhanced Oil Recovery", Journal on Energies, 4:1058-1086.

Carvalho et al. (Feb. 5, 2014) "Evaluation of Solid Content in Petroleum and Water in Oil Emulsion by Ultrasonic Spectroscopy", Revista Virtual de Quimica, 6(2):352-362.

Borges, Gustavo Rodrigues. (2011) "Desenvolvimento De Metodologia Para Avaliação Em Tempo Real De Distribuição De Tamanho De Gota E Teor De Água De Emulsões De Petróleo Sob Pressão (Development of Methodology for Real Time Evaluation of Droplet Size Distribution and Water Content of Pressurized Crude Oil Emulsion)", Programa De Pós-graduação Em Engenharia De Processos—Pep, 111 pages.

* cited by examiner

METHOD FOR ANALYSIS AND DETECTION OF SOLIDS IN EMULSIONS, OIL AND DERIVATIVES THEREOF

CROSS-REFERENCE TO RELATED APPLICATION

This application claims priority to Brazilian Application No. 10 2021 023221 8, filed on Nov. 18, 2021, and entitled "METHOD FOR ANALYSIS AND DETECTION OF SOLIDS IN EMULSIONS, OIL AND DERIVATIVES THEREOF," the disclosure of which is incorporated herein by reference in its entirety.

FIELD OF THE INVENTION

The present invention addresses to a method for analysis and detection of solids in samples of emulsions, oil and derivatives thereof, based on the absorption and scattering of light by solids suspended in solution, with application in situations where the diagnosis of the process is aimed at in order to avoid interface drag (stable emulsions) and allowing the measurement of solids in complex organic samples, even in the presence of high contents of water (>5% v/v).

DESCRIPTION OF THE STATE OF THE ART

Over the years, numerous operational occurrences involving the presence of solids in oil and emulsions have been reported, which resulted mainly in the formation of deposits in various equipment, problems with oil processing and desalination, or accumulation of residues (emulsions) in separation vessels and storage tanks.

Currently, there is no direct way to evaluate the field efficiency of chemical inputs that mitigate the formation of solids, such as scale inhibitors and calcium naphthenates.

The most used method for the determination of solids in oil is the ASTM 4807 standard, which can be briefly described as the mixture of oil with toluene in the ratio of 1:10 (at 90° C.), followed by subsequent filtration. The membrane containing solids is then subjected to drying and weighing to determine the solids content. Although this method is relatively simple, the analysis time can exceed 12 hours, depending on the membrane drying and weighing procedures. Thus, such a procedure is not ideal for monitoring the solids content as a function of the response time. In addition, and not less important, there is the need to disembark a sample for onshore evaluation, due to the need of weighing the membrane obtained in the filtration. Even in procedures carried out in the field (offshore laboratory), there will always be a need to disembark at least the membrane, wash and dry the same. This makes any preventive operational follow-up impossible.

These problems indicated the need for a method to quickly infer the content of solids present in oil and emulsions, in order to enable mitigating or even preventive actions for operational problems arising from the presence of these solids, or to adjust the dosage of chemicals such as scale inhibitors or calcium naphthenates, or even changing the product itself, depending on the level of efficiency.

In the study by BORGES, G. R. (2011) "Desenvolvimento de metodologia para avaliação em tempo real de distribuição de tamanho de gota e teor de água de emulsões de petróleo sob pressão" ("Development of methodology for real-time evaluation of droplet size distribution and water content of oil emulsions under pressure"), Dissertation (Master in Process Engineering), 111f., Tiradentes University—UNIT, Aracaju, S E, a method is developed to carry out online monitoring of the droplet size distribution (DSD) and water content (WC) of oil emulsions in pressurized systems, coupling optical microscopy (OM) and near-infrared (NIR) spectroscopy. All emulsions used were synthesized with an initial water content of 50% (m/m). The models adjusted using the OM as a reference technique for the DSD showed better correlations, and the calibration models obtained for the properties of the pressurized system showed excellent correlations with the experimental data, demonstrating that the technique is an alternative for application in actual process systems, due to its robustness, speed of analysis and precision in the results.

ALVARADO, V.; WANG, X.; MORADI, M. (2011) "Stability proxies for water-in-oil emulsions and Implications in aqueous-based enhanced oil recovery", Energies, v. 4, p. 1058-1086, proposed a literature review on the use of proxies for commonly used emulsion stability and analyzed water-based EOR processes with a focus on heavy oil to contextualize in-situ emulsion stabilization conditions. DLS (Dynamic Light Scattering) is mentioned, which has the advantage of using a small sample volume, in addition to being simple, fast and reliable.

The paper by CARVALHO, R. M. et al. (2014) "Avaliação do teor de sólidos em petróleo e emulsões água em óleo via espectroscopia ultrassônica" ("Evaluation of solids content in oil and water-in-oil emulsions via ultrasonic spectroscopy"), Revista Virtual Química, v. 6, p. 352-362, describes a method based on ultrasonic spectroscopy for measuring solids content in oil and emulsions, in which different masses of silicon oxide are dispersed in oil samples. This work mentions studies indicative of dispersion of solids in oil through the analysis of the calibration curve for quantification of the solids, obtaining the relation between the concentration of solids present in oil in relation to the variation of sound attenuation. The focus of the document in question is related to the use of the ultrasonic spectroscopy tool, while the present invention uses light scattering for the analysis of solids content, thus departing the same from the aforementioned work.

No document of the State of the Art discloses a method for analysis and detection of solids in emulsions, oil and derivatives thereof like this one of the present invention, even in the presence of high contents of water (>5% v/v).

The invention presents a fast method for analyzing solids in samples of emulsions, oil and derivatives thereof, which is based on the absorption and scattering of light by solids suspended in solution. This method can be applied in offshore conditions, allowing a more adequate selection and an optimized control of the use of scale inhibitors and calcium naphthenates inhibitors. For the latter, there are serious limitations in testing and selecting the product in the laboratory, requiring the entire process to be carried out in the field. With the use of the present invention, it becomes possible to select, control and optimize the dosage of the mentioned chemical inputs, in addition to enabling mitigating or even preventive actions for operational problems arising from the presence of solids.

Considering the presence of inorganic solids in general, it becomes possible, with the method of this invention, to control the accumulation at the interfaces of separating vessels, in order to minimize the formation of sludge and possible subsequent problems in the oil BSW and in the OGC of produced water.

The present invention minimizes the effects associated with the formation of interfaces (emulsions) in separation vessels and possible dragging, reducing impacts on the lack of control of OGC for disposal in offshore systems, in particular, avoiding any oily features. In the case of onshore systems, it reduces impacts on the overload of the water treatment system for disposal. Thus, the present invention presents advantages in its application, contributing to greater reliability in terms of control of BSW (oil quality) and OGC (water to be treated and discarded).

BRIEF DESCRIPTION OF THE INVENTION

The present invention addresses to a method for analyzing and detecting solids in emulsions, oil and derivatives thereof, including in the presence of high contents of water (>5% v/v), which is based on the absorption and scattering of light by the solids suspended in solution.

The application of the invention can mitigate the drag of interfaces (stable emulsions), minimizing occurrences of oily features and avoiding overloading of water treatment systems for disposal.

Indirectly, the present invention can be applied in the dosage control of scale inhibitors and naphthenates inhibitors, since such solids tend to concentrate at water-in-oil interfaces. From the quantification of these solids, when present in significant concentrations, the concentration of such products can be increased. At lower concentrations, the dosage of these can be reduced.

BRIEF DESCRIPTION OF THE DRAWINGS

The present invention will be described in more detail below, with reference to the attached figures which, in a schematic way and not limiting the inventive scope, represent examples of its embodiment. In the drawings, there are.

DETAILED DESCRIPTION OF THE INVENTION

The present invention describes a fast method for analyzing solids in samples of emulsions, oil and derivatives thereof, which is based on the absorption and scattering of light by solids suspended in solution. The method allows the measurement of solids in complex organic samples such as oil, even in the presence of high contents of water (>5% v/v).

The light scattering technique is widely used for the quantification of solids in water, but it has strong limitations regarding its use for organic samples, and even more so for oil, because it is dark (low light transmission) and due to the presence of emulsified water. The water droplets emulsified in the oil also cause light scattering, making it impossible to measure solids using this analytical technique, especially in samples with water content greater than 1% v/v.

In addition, the procedures available for measuring solids in oil and emulsions are based on time-consuming gravimetric methods, whose tests can only be carried out in onshore laboratories, which requires disembarking the sample from the offshore platform.

Another feature associated with the present invention is the use of a mixture of solvents, which clarifies the medium and allows the dispersion of oil and emulsified water, thus enabling the transmission of light and, consequently, the measurement of absorption and scattering by solids in suspension.

Further, according to this invention, the calibration curve for quantification of solids is constructed from the variation in absorbance of dispersions of known concentrations of solids in oil, obtained by applying the method of the present invention. This analytical approach makes it possible to measure solids in oil in an offshore environment, even in the presence of high contents of water (>5% v/v).

Traditional methods of quantification of solids in this type of sample are performed only in onshore laboratories, which requires disembarking the sample, with a reasonably long time to obtain results. The advantage of the method of the invention is the use of simple, compact and low-cost instrumentation, which makes it possible to quickly perform analyzes in offshore laboratories.

The solids content is proportional to the difference in the intensity of light absorption (absorbance) of the diluted sample solution, read at a given wavelength of the ultraviolet-visible spectrum, before and after filtration. The absorption of this solution before filtration corresponds to the sum of the absorptions of the insoluble parts and the soluble parts in the solvent plus the fraction of the light scattered by the insoluble parts accounted for as absorbance; meanwhile, the light absorbed by the filtration product is related exclusively to the soluble parts.

Figure 1:
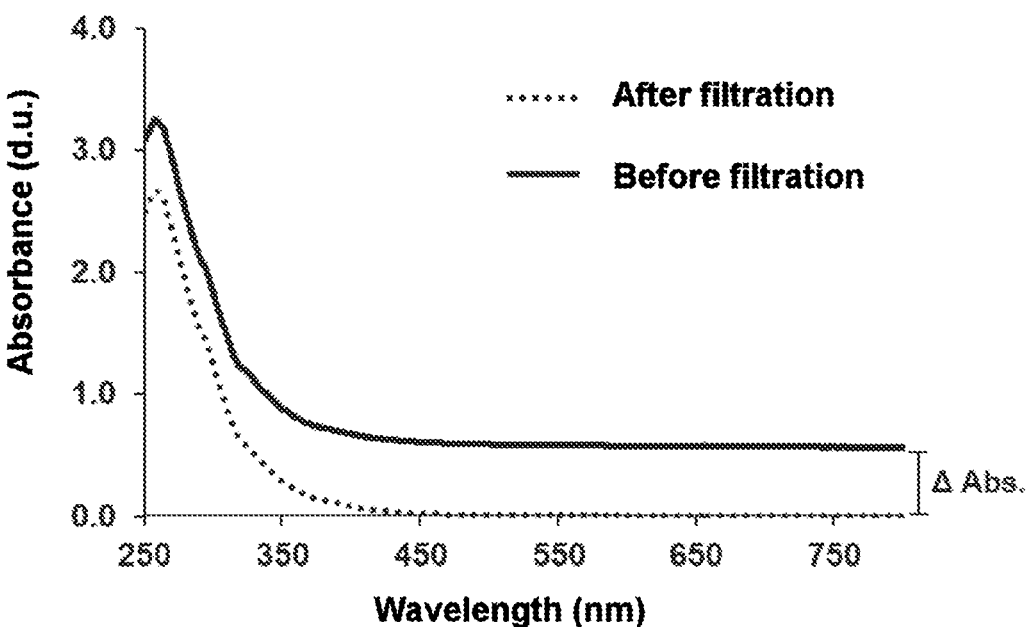
FIG. 1 illustrating UV-visible absorption spectra of a diluted sample solution before (solid line) and after filtration (dotted line)

The difference in the absorbance value under these conditions (before and after filtration), called delta (A) of absorbance, is attributed to the solids present in the sample. FIG. 1 presents absorption spectra in the ultraviolet-visible region and the difference between the absorptions, indicated in the figure as A Abs.

As the absorbance delta (A Abs) is proportional to the concentration of solids in the solution, it is possible to calculate their content in the oil and/or emulsion from a calibration curve. For this, it is necessary to prepare dispersions with known concentrations of solids in oil and to apply the analysis method of the present invention.

Figure 2:
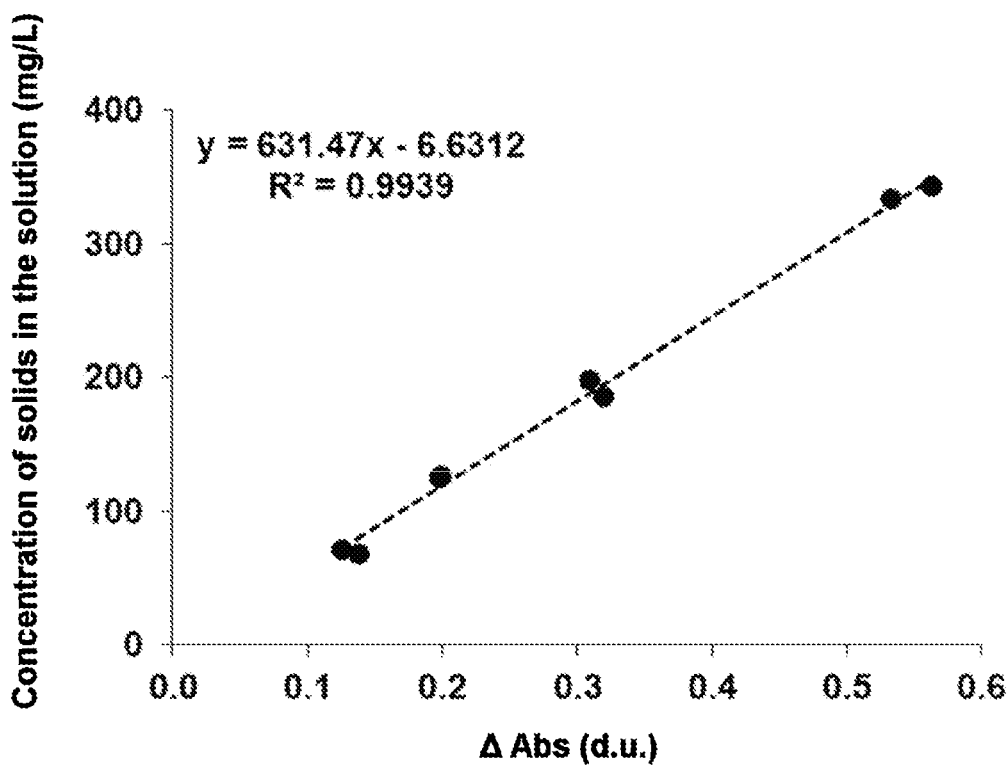
FIG. 2 illustrating an example of a calibration curve correlated to the concentration of solids in the solution as a function of the absorbance delta (A Abs).

FIG. 2 shows an example of a calibration curve. From this, it is possible to calculate the solids content (T), using the equation below:

$$T=(\Delta Abs \times 631.47)-6.6312 \qquad Eq$$

where:
T=solids content in the diluted solution (mg/L).

To calculate the concentration of solids in the sample, use the equation below:

$$C=T \times F \qquad Eq.2$$

Where:
C=concentration of solids in the sample (mg/L);
T=solids content in the diluted solution (mg/L);
F=sample dilution factor.

Knowing the density of the sample, the concentration of solids can also be reported in % mass, using equation 3 below:

$$C = \frac{T \times F}{10000 \times D} \qquad Eq.\ 3$$

Where:
C=concentration of solids in the sample (mg/L);
T=solids content in the diluted solution (mg/L);
F=sample dilution factor;
D=oil density (g/mL).

The method for analysis and detection of solids in samples of emulsions, oil and derivatives thereof comprises the following steps:

(a) The emulsion or oil sample is homogenized for one minute under strong manual agitation;

(b) Next, part of the same is transferred to a wide mouth flask and, with the aid of a syringe, 0.5 to 5 mL of the sample is transferred to a volumetric flask;

(c) A binary mixture of solvents X, an aromatic one (toluene, p-xylene, o-xylene, p-xylene, xylenes, among others) and an oxygenate of the class of glycols (ethylene glycol, butyl glycol, among others), whose concentration of the latter varies from 20 to 80% (v/v), is transferred to the volumetric flask. The concentration of the oxygenated solvent in the solvent mixture must be sufficient to solubilize the water in the oil. The added volume of solvent mixture X must be about 60% of the capacity of the volumetric flask;

(d) The resulting mixture Y is manually agitated for 1 minute and taken to an ultrasound system for 10 minutes to aid in the solubilization of the sample in the solvent mixture X;

(e) The solution is then allowed to stand until it is at room temperature;

(f) Next, the volumetric flask containing mixture Y is filled with solvent mixture X and homogenized;

(g) Next, an aliquot of the Y mixture is taken to read the absorbance in a photometer, using a measuring cell or cuvette with an optical path of at least 10 millimeters;

(h) The absorbance reading is performed at a defined wavelength in the ultraviolet-visible region, using the mixture of solvents X with the absorbance reading blank;

(i) A new aliquot of mixture Y is taken with the aid of a syringe to perform its filtration;

(j) A syringe-type disposable filter is attached to this syringe containing the mixture, with a pore size between 0.45 and 8 μm, and filtration is carried out with the collection of the filtered solution Z. The volume must be enough to fill the cuvette used for absorbance reading;

(k) The absorbance reading of the filtered solution Z is then taken under the same conditions and in the same photometer used for the analysis of the mixture Y;

(l) The difference in the absorbance of the mixture Y minus that of the filtered solution Z corresponds to the absorbance delta (Δ Abs), and this is attributed to the solids present in the sample, whose concentration can be calculated from a calibration curve such as exemplified in FIG. 2;

(m) By determining the concentration of solids in the mixture Y, it is possible to calculate the solids content in the sample from the dilution factor of the mixture Y. The dilution factor is the ratio between the capacity of the volumetric flask used in the preparation of the mixture Y is the sample volume used in the analysis;

(n) The solids concentration in the sample is the product of the solids content in the mixture Y and the calculated dilution factor.

EXAMPLES

The following examples are presented in order to more fully illustrate the nature of the present invention and the way to practice the same, without, however, being able to be considered as limiting its content.

Field analyzes were carried out in a refinery and offshore production platform from samples collected at desalter interfaces and separation vessels respectively (in a field laboratory). Additionally, samples were also collected for analysis at an external laboratory and the obtained results were compared. Adherence was observed between the obtained data, making it possible to obtain a solids distribution profile along the vessel or desalter.

In addition, collections were carried out on different dates, making it possible to verify sensitivity in terms of variation and influence of operational actions in changing the amounts of solids observed. The same type of comparison was also extended to oil samples, with good correlation between measurement via gravimetry and the approach of the present invention.

Table 1 below presents, as an example, the comparison of results of the quantification of solids by gravimetry (traditional method) and the method proposed in the present invention.

TABLE 1

| Results of the quantification of solids in emulsion and oil samples by the traditional gravimetric method and by the method of the present invention. | | | | | | |
|---|---|---|---|---|---|---|
| Sample Type | Emulsion | Emulsion | Emulsion | Emulsion | Oil | Oil |
| Gravimetry (% mass) | 0.3 | 0.3 | 1.1 | 0.4 | 0.2 | 0.1 |
| Proposed method (% mass) | 0.4 | 0.3 | 1.0 | 0.6 | 0.2 | 0.1 |

It should be noted that, although the present invention has been described in relation to the attached drawings, it may undergo modifications and adaptations by technicians skilled on the subject, depending on the specific situation, but provided that within the inventive scope defined herein.

The invention claimed is:

1. A method for analysis and detection of solids in emulsions, oil and derivatives thereof, comprising the following steps:

(a) homogenizing an emulsion or oil sample for one minute under strong manual agitation;

(b) transferring part of the emulsion or oil sample to a wide mouth flask and, with a syringe, transferring from 0.5 to 5 mL to a volumetric flask;

(c) transferring a binary mixture of solvents X comprising an aromatic solvent comprising toluene, p-xylene, o-xylene, xylenes, or combinations thereof and an oxygenate of a glycol class comprising ethylene glycol, butyl glycol, or combinations thereof into the volumetric flask, wherein the added volume of solvent mixture X is 60% of the capacity of the volumetric flask;

(d) manually agitating the resulting mixture Y for 1 minute and placing the same in an ultrasound system for 10 minutes;

(e) allowing the mixture Y to stand until it reaches room temperature;

(f) filling up the volumetric flask containing the mixture Y with the mixture of solvents X and performing its homogenization;

(g) taking an aliquot of the mixture Y to read absorbance in a photometer, using a measuring cell or cuvette;

(h) taking the absorbance reading at a defined wavelength in an ultraviolet-visible region, using the solvent mixture X as a blank for the absorbance reading;

(i) taking a new aliquot of the mixture Y with a syringe to perform its filtration;

(j) attaching a disposable filter to the syringe containing the mixture Y and proceeding to filtration with the collection of the filtered solution Z, in which the volume is enough to fill the measuring cell or cuvette used for absorbance reading;

(k) performing the absorbance reading of the filtered solution Z under the same conditions and in the same photometer used for the analysis of the mixture Y;

(l) determining solids content from a calibration curve, through a difference of the absorbance of the mixture Y minus that of the filtered solution Z, which corresponds to the absorbance delta (Δ Abs); and (m) determining a concentration of solids in the mixture Y and calculate the solids content in the emulsion or oil sample from a dilution factor of the mixture Y.

2. The method of claim 1, wherein a concentration of the oxygenate of the glycol class varies from 20 to 80% (v/v).

3. The method of claim 1, wherein the measuring cell or cuvette has an optical path of at least 10 millimeters.

4. The method of claim 1, wherein the disposable filter is of a syringe type and has a defined pore size between 0.45 and 8 μm.

5. The method of claim 1, wherein the dilution factor is a ratio between the capacity of the volumetric flask used in the preparation of the mixture Y and the volume of emulsion or oil sample used in the analysis.

6. The method of claim 1, wherein the concentration of solids in the emulsion or oil sample is a product of the solids content in the mixture Y and the dilution factor.

7. The method of claim 1, wherein the emulsion or oil sample has water content above 5% v/v.

* * * * *